United States Patent
Sun et al.

(10) Patent No.: US 10,783,711 B2
(45) Date of Patent: Sep. 22, 2020

(54) SWITCHING REALITIES FOR BETTER TASK EFFICIENCY

(71) Applicant: International Business Machines Corporation, Armonk, NY (US)

(72) Inventors: Lin Sun, Cary, NC (US); Liam S. Harpur, Skerries (IE); Matthew E. Broomhall, Goffstown, NH (US); Paul R. Bastide, Boxford, MA (US)

(73) Assignee: International Business Machines Corporation, Armonk, NY (US)

( * ) Notice: Subject to any disclaimer, the term of this patent is extended or adjusted under 35 U.S.C. 154(b) by 2 days.

(21) Appl. No.: 15/891,008

(22) Filed: Feb. 7, 2018

(65) Prior Publication Data

US 2019/0244427 A1    Aug. 8, 2019

(51) Int. Cl.
| | |
|---|---|
| *A61B 5/16* | (2006.01) |
| *G06F 3/01* | (2006.01) |
| *G06T 19/00* | (2011.01) |
| *G06F 19/00* | (2018.01) |

(52) U.S. Cl.
CPC ............ *G06T 19/006* (2013.01); *A61B 5/165* (2013.01); *G06F 3/011* (2013.01); *G06F 19/00* (2013.01)

(58) Field of Classification Search
CPC ...... G02B 2027/0138; G02B 2027/014; G02B 2027/0178; G02B 27/017; G02B 27/0172; G06K 9/00335; G06K 9/00671; G06F 11/3438; G06F 11/3452; G06F 3/048; G06F 8/38; G06F 9/44505; G06F 9/451; G06F 3/04815; G09G 5/377; G06T 19/006

USPC ........................................................ 345/633
See application file for complete search history.

(56) References Cited

U.S. PATENT DOCUMENTS

| | | | |
|---|---|---|---|
| 2007/0207448 A1 | 9/2007 | Glaser et al. | |
| 2014/0139551 A1* | 5/2014 | McCulloch | .......... G02B 27/017 345/633 |
| 2015/0262425 A1* | 9/2015 | Hastings | ............ G02B 27/0172 345/633 |

(Continued)

OTHER PUBLICATIONS

Chittaro et al., "Adaptive 3D Web Sites", Book, The Adaptive Web, LNCS 4321, pp. 433-463, 2007, Springer-Verlag Berlin Heidelberg 2007.

(Continued)

*Primary Examiner* — Jin Cheng Wang
(74) *Attorney, Agent, or Firm* — Scully, Scott, Murphy & Presser, P.C.; Michael O'Keefe, Esq.

(57) ABSTRACT

An intelligent recommendation system and method for suggesting users perform various tasks in different reality systems to help user to maximize their productivity and achieve better satisfaction. By recognizing that a user is not efficient or unable to perform tasks well in real reality, the system suggests that the user try doing the similar task in a virtual reality (VR) or augmented reality (AR) environment and effects a physical switching to that environment for the user to practice and improve user's skill on the tasks. Further, by recognizing that user's emotions (e.g., sad or bad mood), the system further suggests the user to do certain things in the VR or AR environment to improve user's mood. The system and method continuously suggests performing tasks in VR or AR as needed, based on user's task efficiency score in real reality and any improvement occurred in RR when doing the task in VR.

20 Claims, 6 Drawing Sheets

(56) References Cited

U.S. PATENT DOCUMENTS

2017/0116337 A1 4/2017 Creamer et al.
2018/0117769 A1* 5/2018 Delazari Binotto ... B25J 9/1694
2018/0314980 A1* 11/2018 Osotio .................. G06N 20/00

OTHER PUBLICATIONS

Sims, "Reusable, lifelike virtual humans for mentoring and role-playing." Computers & Education vol. 49, Issue 1 Aug. 2007: pp. 75-92.

Wang et al. "Character agents in E-learning interface using multimodal real-time interaction." Human-Computer Interaction. HCI Intelligent Multimodal Interaction Environments (2007), 12th International Conference on Human-Computer Interaction, Beijing, Jul. 22-27, 2007, pp. 225-231.

* cited by examiner

| | |
|---|---|
| 505 — Context_Scenario | Switch Realities --> Business Report -> Coffee Shop |
| 510 — Augmented_Contents | Coffee, Business Revenue Goal |
| 515 — Insert_Time | When conversation starts between the meeting attendees at the meeting location |
| 520 — Meeting_Attendees | UserA & UserB |
| 525 — Meeting_Location | Coffee Shop |
| 530 — Meeting_Content | UserA's Business Report |
| 535 — Measured_Task_efficiency_in_AR | Time to finish the business report (1.5 days) & overall business report review result evaluation score from supervisor (score: 85) |
| 540 — Historical_Task_Efficiency_in_RR_from_history | Time to finish the business report (2 days) & overall business report review result evaluation score from supervisor (score: 70) |
| 545 — UserID | UserA_50 |
| 550 — Remove_AR_VR_Contents | As meeting attendees leave the meeting location or switch to other content than the meeting content |
| 555 — Should_AR_Used | Yes |
| 560 — Should_VR_Used | No |
| 565 — Recommend_AR_In-Future_For_This_Context | Yes |
| 570 — Recommend_VR_In-Future_For_This_Context | No |

SWITCHING REALITIES FOR BETTER TASK EFFICIENCY

FIELD OF THE INVENTION

The present invention relates generally to recommender systems, platforms or engines for recommending different activities to be performed by a user in different environments, e.g., a virtual reality environment, a real reality environment or an augmented reality environment, and switching to those environments, to achieve a better satisfaction and efficiency.

BACKGROUND

Occasionally, a user can experience and have great emotion swings in "real" time. A user may find oneself capable of doing certain tasks very well in "real" reality and some tasks very badly or incapable of doing them at all.

SUMMARY OF THE INVENTION

An embodiment of the present invention is a system, method and computer program product for enabling a user to perform tasks in other "realities," e.g., virtual reality, real reality or augmented reality, so that the user may achieve a better or increased task performance efficiency and/or user satisfaction.

An intelligent recommendation system, method and computer program product that suggests users to do various tasks in different reality systems to help user to maximize the productivity and achieve better satisfaction, happiness and health.

In one aspect, there is provided a task recommender tool. The task recommender tool comprises: a memory storage system storing program instructions; a processor for running the stored program instructions to configure the processor to: detect a user's task efficiency in performing a task; recommend, based on a results of the task efficiency detecting, a computing environment switch from a current real environment to one of: a virtual reality computing environment or an augmented reality computer environment, recommend a task to performed in the switched computing environment, wherein upon switching to a switched computing environment, the user performs the recommended task in the switched environment, determining whether the user's efficiency in performing the task has increased, and repeating the task efficiency detecting in each subsequent real or a switched environment while the user performs the recommended task in the real or switched environment until the user's task efficiency has improved.

In a further aspect, there is provided a method for recommending tasks for a user to perform. The method comprises: detecting, by a processor, a user's task efficiency in performing a task; using the processor to recommend, based on a results of the task efficiency detecting, a computing environment switch from a current real environment to one of: a virtual reality computing environment or an augmented reality computer environment, and using the processor to recommend a task to performed in the switched computing environment, wherein upon switching to a switched computing environment, the user performs the recommended task in the switched environment, determining, using the processor, whether the user's efficiency in performing the task has increased, and repeating the task efficiency detecting in each subsequent real or a switched environment while the user performs the recommended task in the real or switched environment until the user's task efficiency has improved.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 5 depicts an example table 500 having several example variables and values used in the various modules of FIG. 3 for governing the example scenario described;

DETAILED DESCRIPTION

The present invention is directed to computer-implemented system and methods that provide a recommendation to suggest users do various tasks in different reality systems, e.g., augmented reality (AR), virtual reality (VR), and real reality (RR) to help the user to increase productivity and achieve better satisfaction, happiness and health. AR/VR systems might include, for example, annotations of real items in the environment, additional annotations to reports being viewed, and other helpful information.

For example, based upon results of monitoring user efficiency in accomplishing a task in a real reality, the systems and methods enable the user to transit to a virtual or augmented reality based on that user's observed efficiency.

Figure 1:
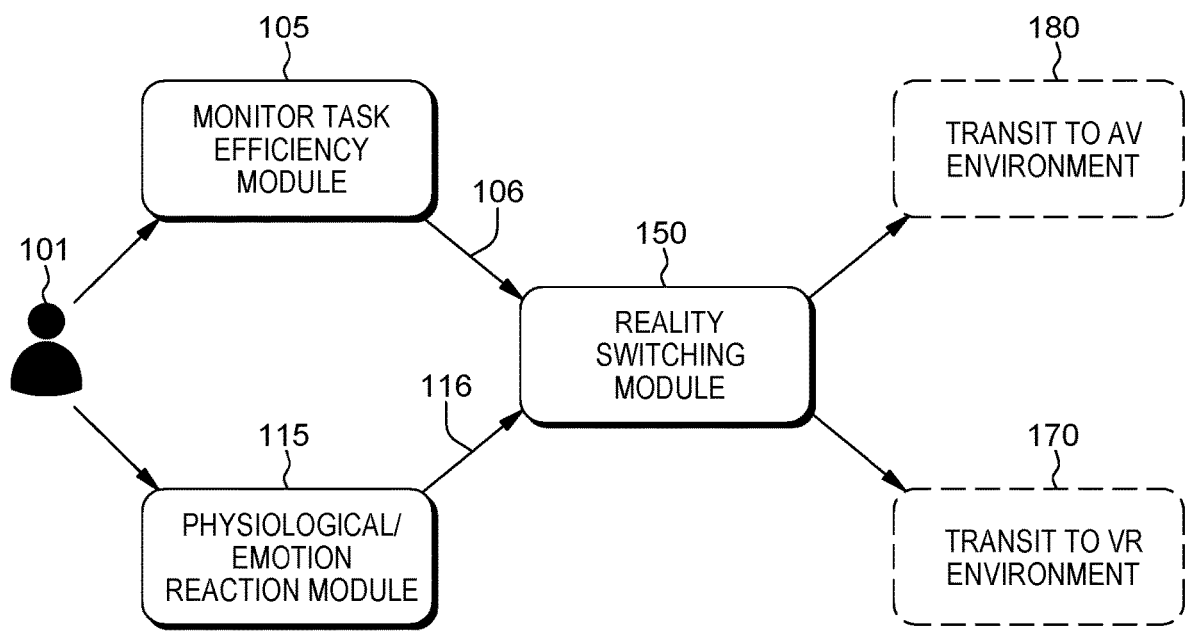
FIG. 1 depicts a conceptual implementation of a system for switching realities in one aspect of the invention.

FIG. 1 depicts a conceptual implementation of a system 100 for switching realities in one aspect of the invention. As shown, a user 101 is performing a task in real-time, i.e., in a real reality state. The task could be anything which may be analyzed and evaluated for determining an efficiency. The user's actions are monitored by a monitoring device 105 that may measure the user's task efficiency. Monitoring device 105 may include any device that may be used to monitor human performed tasks, e.g., a particular type of activity in a particular domain specific setting, e.g., finance, healthcare.

For example, one task that may be monitored for efficiency is performing a particular type of surgery or learning how to use a piece of equipment or learn how to use a computer program. Another task may be to generate certain code for a computer to perform a task or navigate an interface for accomplishing tasks. It is understood that certain tasks are easy to be monitored than others. For example, tasks directly performed on a computer or devices are much easier to monitor and determine user's efficiency. Certain tasks may even have inherently have a scoring scheme, along with schemes for comparison with others.

In one embodiment, certain tasks can be monitored indirectly via social network sites such as Twitter®, Facebook® or IBM® Connections™. Use of artificial Intelligence tools such as provided by International Business Machine's Watson® (such as Watson® Personality Insight, Watson® Tone Analyzer, etc.) may be used to infer the user's personality characteristics, e.g., based on that user's digital communications such as email, blogs, tweets, and forum posts. These tools can be used here to mine the data to determine user's efficiency and emotions around a given task, e.g., as they may be posted on the social network sites.

In one embodiment, tasks can also be interest vectors, i.e., topics or keywords that may be of interest. For example, a calendar event for "yearly review" might be an interest vector and the system will ascertain whether it is of enough impact to study further with a view to possibly switch reality when engaged in that keyword/topic. Interests can be mined from any personal data store such as email or social networks or messaging applications.

Any task that may be performed by a user in these switched environments is contemplated if the task has a better result (e.g., happiness as measured by the tone of subsequent communication, a facial expression, or some other measure) in a certain environment.

Such efficiency task module 105 may employ techniques that monitor efficiency of the user 101, e.g., measuring and determining a time it takes the user to execute a task or multiple tasks/activities, and other aspects such as determining a user's response time or determining any errors performed by the user. This monitoring data 106 may be correlated to create knowledge for understanding the particular user's efficiency.

In one embodiment, the system 100 at the task efficiency module 105 may generate a task efficiency score for the user based on the monitoring data to help easily calculate user's task efficiencies over time.

During the monitoring of the user 101 in performing the task, further sensors may be actuated to capture and store the user's physiological/emotional response and generate corresponding physiological/emotion response data 116 with a timestamp indicating the particular time a task or an aspect of the task was performed. For example, as shown at 110, while the subject is performing a task, the user's activities are captured by a sensor. In one embodiment, such a sensor may be a video capture device (e.g., a digital video-camera) that that captures as a video, the subject's attitude or emotion while performing the task. The system may employ a classifier device (not shown) that receives as input the user's task being monitored and the sensed video of the user's emotion. The classifier device is configured to recognize the user's emotion corresponding to the user's physiological response captured in the video. In one embodiment, the recognizing of emotions may be based on observed facial and/or voice (speech) clues. Thus, the system gains additional insight or clue into exactly how the user 101 is feeling when performing a task.

As further shown in FIG. 1, in one embodiment, a reality switching module 150 receives the monitored user's task efficiency data 106 from monitor module 105 and further receives user emotions data 116 around performing the tasks.

Logic executed in reality switching module 150 determines whether the user 101 is efficient or not efficient or unable to perform certain tasks well in real reality. This may be based on logic that correlates a determined user task efficiency score, e.g., a long time to perform, and a corresponding detected emotion(s), e.g., frustration, anger, nervousness, etc.

In one embodiment, a statistical measure may be used for determining at what efficiency/emotion would require a suggested reality change. For example, a method may be employed that uses a bell curve whenever the system states that a recommendation is given at 70% efficiency in another reality.

Upon recognizing that user is not efficient or unable to perform certain tasks well in real reality, the reality switching module 150 suggests that the user try doing the similar task in a virtual reality (VR) system 170 or an augmented reality (AR) system 180 providing the tools and interfaces to practice and improve user's skill on the tasks. For example, by recognizing that user is in a bad mood such as being angry, sad or mad, etc., the system 100 suggests to the user to do certain things in VR or AR to improve user's mood. In one embodiment, the reality switching module 150 may output a suggestion via a display interface to perform the task in the other VR or AR system.

The system 100 then employs the same monitoring and sensing tools 105, 115 to monitor the user's task efficiency for each AR and/or VR reality to see if the user 101 improves the efficiency. The results of the monitored data are leveraged to suggest that the user do certain tasks in real reality and certain tasks in VR or AR.

A non-limiting illustrative example is now presented. In the example, a user, e.g., UserA, tends to write up a business report in VR system environment better than in (real) reality, because the VR environment represents each of key points that userA must focus to win the business report, plus with UserA's desired surroundings to allow UserA to excel.

Further, as a non-limiting example, a group of users, e.g., GroupB, performs their Business innovation session better in AR system environment because the AR environment represents each of key points that GroupB must focus on to produce innovative sessions.

Figure 2:
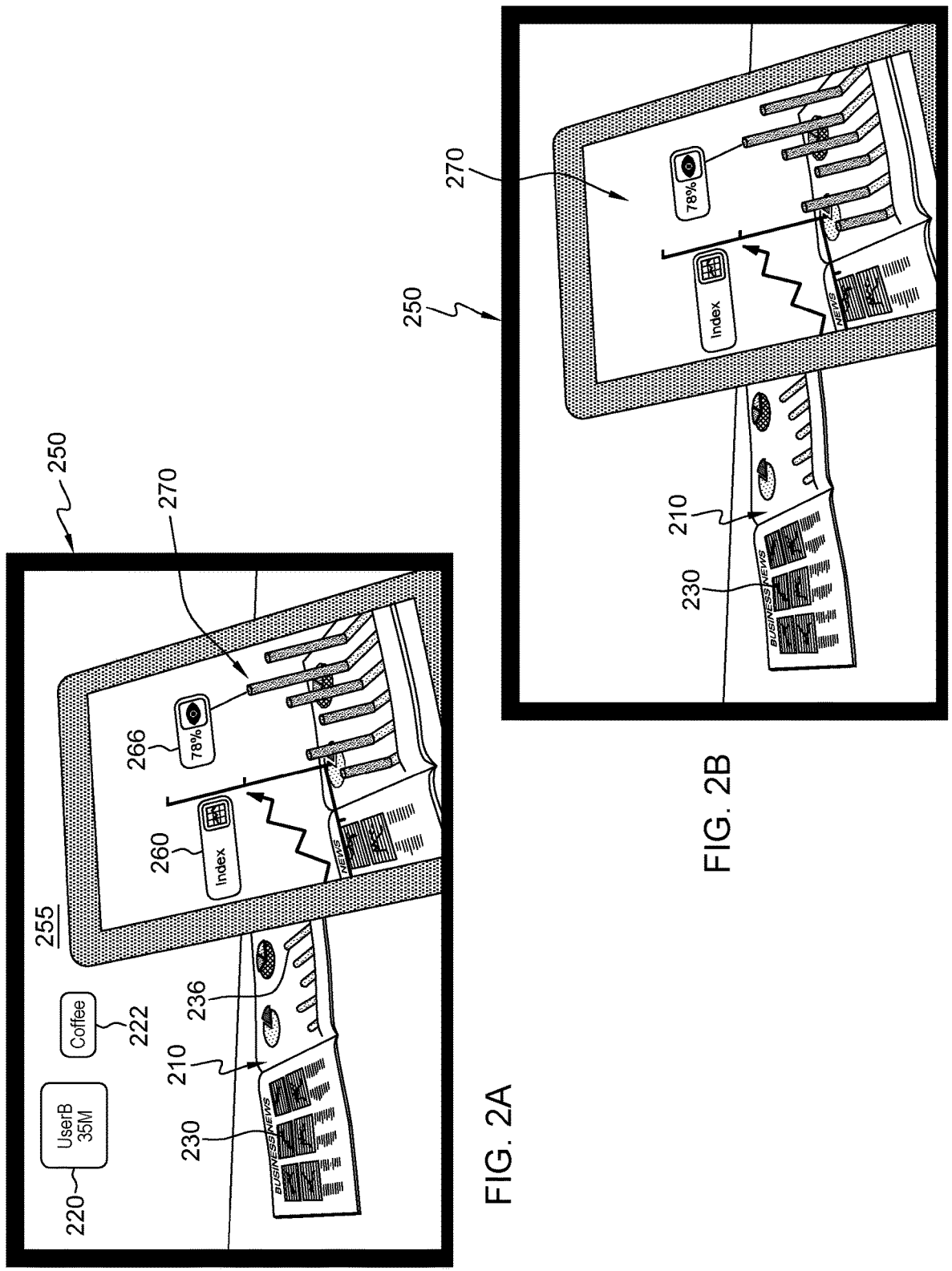
FIG. 2A depicts an example scenario in which a first user, UserA, is at an augmented reality (AR) computing environment in the form of a coffee shop meeting with a second user, UserB, in the example depicted.
FIG. 2B depicts the resulting example scenario of FIG. 2A in which the conversation shifts and UserB's label disappears as the needs of the conversation change in the example depicted.

As shown in FIG. 2A, in a further non-limiting example, a first user, UserA, is at a coffee shop premises 201 meeting with a second user, UserB, to discuss a business report 210. The UserB uses a tool such as a smart pad, smart phone, table or like other computing device 250. When imagined as being in the coffee shop, the system 100 uses an augmented reality (AR) system to start labeling everything within eye sight on the UserB device 250. In one embodiment, the AR system may be programmed to generate and visually present annotations of real items in the environment, additional annotations to reports being viewed, for example.

Thus, as shown via the display interface 255 at device 250, there is generated an AR system for visual presentation via the display interface 255, one or more labels such as label 220 to highlight they are in the coffee shop and a label 222 to highlight that UserB is reviewing the report 210. Other labels 260, 266 may be generated on the graphic/chart corresponding to the report content as presented on a user computing device, e.g., tablet 270, to highlight for the UserA the corresponding sections 230, 236 in the report 210 while reviewing the report in the AR environment. In this manner, the UserA may gain additional understanding of the 210 report contents.

As shown in FIG. 2B, as the conversation shifts with UserB, the AR label 222 are terminated and disappear from view, and UserB's label 220 disappears as the needs of the conversation change.

Figure 3:
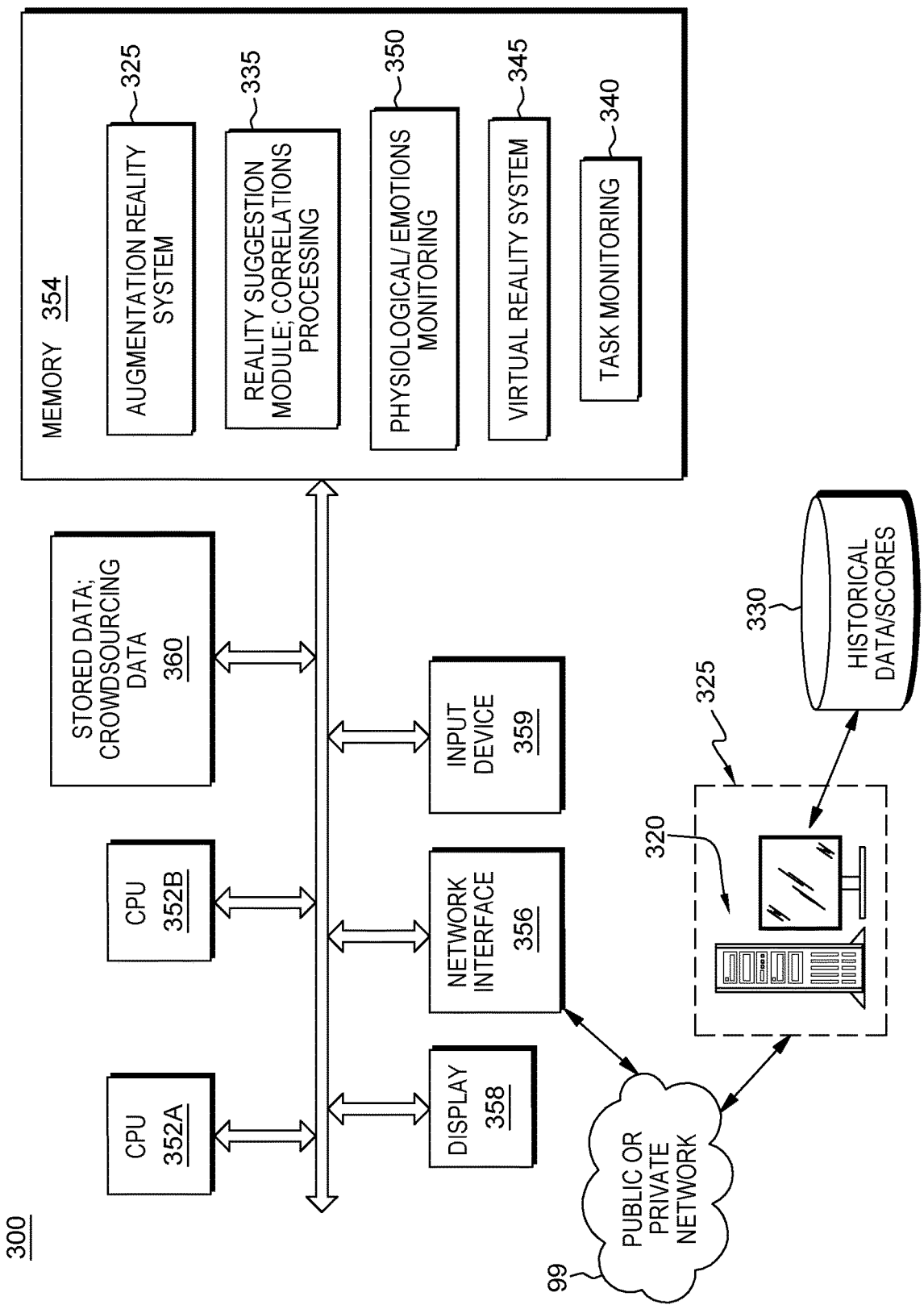
FIG. 3 depicts a system in which the present invention is employed according to an embodiment.

FIG. 3 depicts a detailed embodiment of a computer system 300 for recommending a switching of realities. In some aspects, system 300 may include a computing device, a mobile device, or a server. In some aspects, computing device 300 may include, for example, personal computers, laptops, tablets, smart devices, smart phones, or any other similar computing device.

Computing system 300 includes one or more processors 352A, 352B, a memory 354, e.g., for storing an operating system and program instructions, a network interface 356, a display device 358, an input device 359, and any other features common to a computing device. In some aspects, computing system 300 may, for example, be any computing device that is configurable to communicate with a web-site 325, a web- or cloud-based server 320, or with other computing devices, e.g., IBM's Watson®, over a public or private communications network 99. Further, as shown as part of system 300, data such as task efficiency data, for later usage by the user or for crowd sourcing application, may be stored locally in an attached memory storage device 360, or otherwise may be stored in a remote memory storage device 330, e.g., a database, and accessed via a remote network connection for input to the system 300.

In the embodiment depicted in FIG. 3, processor 352A, 352B may include, for example, a microcontroller, Field Programmable Gate Array (FPGA), or any other processor that is configured to perform various operations. Processors 352A, 352B may be configured to execute instructions as described below. These instructions may be stored, for example, as programmed modules in memory storage device 354.

Memory 354 may include, for example, non-transitory computer readable media in the form of volatile memory, such as random access memory (RAM) and/or cache memory or others. Memory 354 may include, for example, other removable/non-removable, volatile/non-volatile storage media. By way of non-limiting examples only, memory 354 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 356 is configured to transmit and receive data or information to and from a server 320, e.g., running Watson®, or a web-based server running a social media web-site, via wired and/or wireless connections. For example, network interface 356 may utilize wireless technologies and communication protocols such as Bluetooth®, WWI (e.g., 802.11a/b/g/n), cellular networks (e.g., CDMA, GSM, M2M, and 3G/4G/4G LTE), near-field communications systems, satellite communications, via a local area network (LAN), via a wide area network (WAN), or any other form of communication that allows computing device 300 to transmit information to or receive information from the server 320.

Display 358 may include, for example, a computer monitor, television, smart television, a display screen integrated into a personal computing device such as, for example, laptops, smart phones, smart watches, virtual reality headsets, smart wearable devices, or any other mechanism for displaying AR, VR information to a user. In some aspects, display 358 may include a liquid crystal display (LCD), an e-paper/e-ink display, an organic LED (OLED) display, or other similar display technologies. In some aspects, display 358 may be touch-sensitive and may also function as an input device.

Input device 359 may include, for example, a keyboard, a mouse, a touch-sensitive display, a keypad, a microphone, or other similar input devices or any other input devices that may be used alone or together to provide a user with the capability to interact with an augmented reality computing environment and virtual reality computing environment generated at the computing device 300.

In one embodiment, programmed processing modules stored in a device memory 354 provide the system with abilities for monitoring and detecting users' task efficiencies in any reality environment and recommending switching realities based on information from a user's task performance monitoring flow 106 and/or corresponding emotional reactions data flow 116.

As shown in FIG. 3, in one embodiment, a task monitoring module 340 is provided that invokes operations for monitoring aspects of the user's executing or performing a task in the particular domain and detect a user task efficiency. For example, this module 340 may be used to measure particular time durations for a user performing a particular task or detect errors in the task performance. The task monitoring module 340 is configured to monitor the task in any reality environment, i.e., real, augmented and/or virtual, analyze and evaluate a user efficiency and for generating the efficiency task data 106 such as an efficiency score.

In one embodiment, module 340 may generate a user's task efficiency score based on a combination of sources where each source may weight differently. For example, a direct score computed by the computer may weigh higher than from a social media web-site generated score. In one embodiment, a task efficiency score can be generated based on the length (of time) it takes to perform the task (x), the numbers of errors/failures (y) when performing the task, the number of pauses or interruptions (z) taken, the number of task completion results, etc. (t). Based on these values, a simple algorithm for generating a task efficiency score may be a relation such as y*z*t/x.

In one embodiment, a "low" task efficiency score may be determined as one that is lower (e.g., a certain percentage lower) as compared to average scores, e.g., historical average scores. In this embodiment, the system can collect scores over time and determine average scores over time based on past historical data obtained from the system 300.

As further shown in FIG. 3, one program module stored in a device memory 354 may include a physiological emotions monitoring module 350 that when run by a processor device, configures the system to obtain and process sensor data 116 from sensors monitoring devices used for detecting emotions or physiological behavior of the user while performing the task in any reality environment, i.e., real, augmented and/or virtual, and analyze and evaluate a user's emotions and for generating the corresponding user emotion data 116. The emotion data 116 may indicate a sad/bad mood or a happy/elated mood for example as determined by one or more of: facial analysis, voice analysis and social media comments/updates from the user. For example, a user's frustration may be determined by running a facial analysis (e.g. obtained from a video camera or like recorder although other monitoring sensor devices. In an embodiment, a audio/video recording device is controlled by running the instructions in the physiological emotions monitoring module for monitoring physiological behavior of the user and detecting an emotional state using techniques known in the art. As an example, a user's expression of frustration can be determined by user's frequent stops/interruptions when performing the task, or may be inferred from a low task efficiency score.

Alternately or in addition, the user's voice may be recorded and a voice analysis conducted for evaluating the user's emotion state.

In an embodiment, the system may interface with the Watson® Tone analyzer system to determine the tone of the user's social media and forum messages and determine if the user is in a frustrated emotional state.

Alternately or in addition, the user's emotional state may be inferred based on that user's social media comments/updates and/or social media comments/updates from that user's contacts.

As further shown in FIG. 3, one program module stored in a device memory 354 is the reality switching module 335 which receives the efficiency data flow 106 for that user and the physiological reactions/emotion data flow 116 and invokes operations for analyzing these data for determining a user efficiency and/or mood, and whether to recommend to the user to change or switch performing of the task in another reality.

In one embodiment, the reality switching module may generate and/or make use of "crowdsourced" data of AR/VR suggestions stored in memory 330 or 360 for same/similar tasks for making suggestions to the user.

As further shown in FIG. 3, one program module stored in a device memory 354 may include the augmentation reality system module 325 for use in generating at the computing system, an augmented reality interface for the user to interact with to perform the task in response to a reality change suggestion. Similarly, program module stored in a device memory 354 may include the virtual reality system module 345 for use in generating at the computing system, a virtual reality environment interface for the user to interact within to perform the task.

Figure 4:
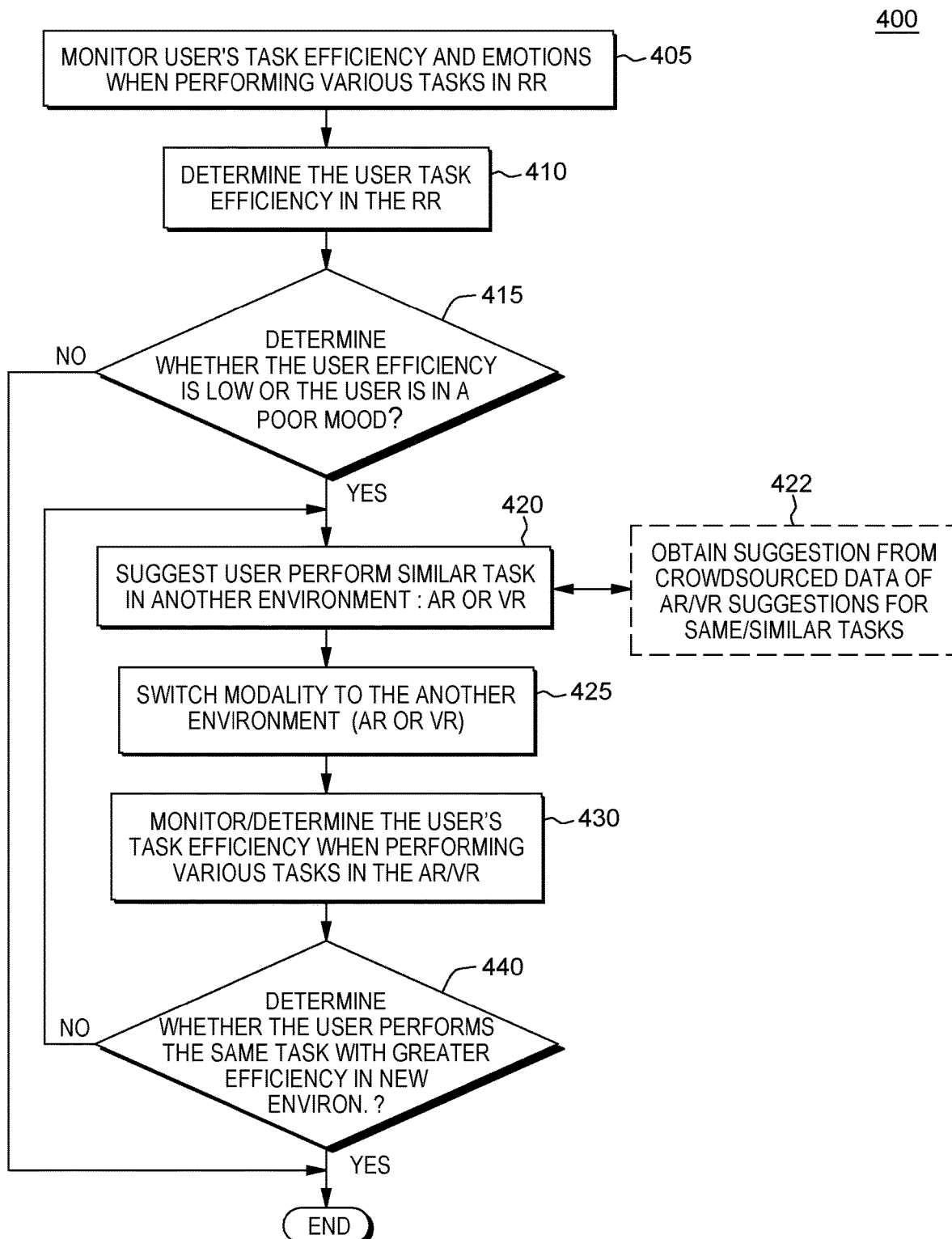
FIG. 4 depicts a method of operating the intelligent recommendation system to switch realities using the computer system of FIG. 3.

FIG. 4 depicts a method of operating the intelligent recommendation system to switch realities using the computer system of FIG. 3.

As shown at first step 405, the task monitoring module 340 monitors a human subject 101 performing a task in a particular domain. In an example embodiment, the user in real reality (RR) environment, may be performing a task such as analyzing data and generating a business report for a particular use or purpose. Concurrently, the physiological/emotions monitoring module 350 and associated sensors are used for monitoring emotions of the user 101 while performing the task in the particular domain.

At 410, the correlations processing at the Reality Switching module 335 is used to determine the user task efficiency in the RR when performing the task. Then, at 415, the reality switching module 335 determines whether or not the subject user's task efficiency is either low (not high), or whether the user is sensed as being in a poor mood. If the user's task efficiency is either low, or the user is detected as being in a poor mood, then at 420 the reality switching module 335 suggests that user perform similar task in a VR (or AR) environment. Otherwise, at 415, the process will end as the user is determined as being efficient (e.g., meeting a high efficiency score threshold) and in a good emotional state of being.

At 415, one or more methods can be used to determine whether a suggested task in a VR is needed: User has been frustrated about certain tasks by monitoring the user; the user has been getting low task efficient score; the user has not been able to improve on the low task efficient score; and/or the user is intimated about surrounding users watching or providing feedback in real reality.

As shown in FIG. 4, at 420, based on the evaluation of a user's task efficiency, the system may determine, at 422, from "crowdsourced" data and/or historical data obtained over time, a recommendation or suggestion to switch to AR environment or VR environment for performing the same/similar tasks. In this aspect, the determination of whether to recommend switching to an VR/AR environment will be based on past history of crowd sourcing and on which reality is best to aid user's efficiency in learning a certain task. Thus, different tasks can lead to a different reality suggestion, and the historical data will help the system to decide which reality should be recommended.

Thus, in an embodiment, the system switching module 335 may resolve or set a variable value "should_AR_used" or alternately a variable "should_VR_used," that is a generated value based on user's situation and data. The generated value can be based on the given data and historical data in the past for the task and task efficiency score along with the reality indicated from crowd sourcing information.

The crowdsourcing information may be obtained by recording the user's computed efficiency scores over time along with VR activities that user has performed to determine if there is any correlation of using VR to improve the user's task efficiency score. Additionally recorded may include the time length of help from VR sessions per a given task type and/or the number of VR sessions per a given task type.

Subsequent use of this recorded user information as crowd sourcing data, the system 300 may leverage the crowd sourcing data to further aid the system's decision on the switching module. For example, based on the number of VR sessions recorded for a given task type, the system may check whether the suggestion of performing the task in virtual reality environment actually helped for a given type of user(s) and the degree of help.

As a further example of subsequent use of this recorded user information as crowd sourcing data, based on the number of VR sessions recorded for a given task type, the system 300 checks whether the suggestion of performing which task in virtual reality actually helped and the degree of help.

As a further example of subsequent use of this recorded user information as crowd sourcing data, based on the number of VR sessions recorded for a given task type, the system 300 determines when users can do the task effectively without help from virtual reality or augmented reality environments.

Thus, the system 300 continuously suggests performing task in VR as needed, based on user's task efficiency score in real reality (RR) and any improvement occurred in RR when doing the task in VR.

If the reality switching module 335 determines that the user's efficiency needs to be improved and suggests the switching of the user to perform the same or similar task in AR or VR environment, then the system will responsively "switch" to the new AR or VR environment modality at 425.

In one embodiment, the physical switching from a user's current environment (e.g., RR) to a new AR or VR computing environment first involves the creation of a configuration file for storage and invocation at the particular AR/VR device. The configuration file may specify relevant objects of interest to be present in the switched to environment, e.g., "<background-color: #93B874; >. Such objects of interest include but are not limited to: any UI change be it either visual, audio, haptic or any such change. For example, for the visual category, a small subset could be "report" in an AR environment, set forth in the configuration file as follows:
AR_Report={"color": [255,255,0,255], "size": 5, "type": "report", "style": "Circle" } for coordinates (lat,lon,title, content)

The determining of which objects are to be configured for the switched-to reality environment, is a function of the task being learned, e.g., in the same way that a user currently configures for a context, the system does the same. An example logic employed at the switched-to business innovation session AR system environment device of FIG. 2A to specify the objects for the example environment may include:
IF (Metrics_Meeting_Context==TRUE) THEN (DISPLAY AR_ReportObjects)

Subsequent to the "switch" recommendation being made to the switched environment, the reality switching module 335 will signal the particular computing device implementing the AR/VR to implements a "cut-over", i.e., a loading of the configuration file and objects to generate the full AR/VR interface on a computing device. In one embodiment, the AR/VR computing device is primed such that the amount of time (i.e., "cut-over" time) it takes to load the full AR/VR interface is improved once a "switch" recommendation is made using the created configuration file. In one embodiment, the "loading" of the AR/VR environment is hidden from the user and performed in the background if it is likely (the "threshold") that it will be needed That is, the AR/VR device runs the computing necessary to generate the AR/VR but merely does not display the new environment to the end user. If a statistical probability of "switching" reality is increasing towards the threshold, then the backend computing is executed and the AR/VR device will then implement the cut-over. In order to generate a rich AR/VR environment, the AR/VR device may not have enough computing resources and such may rely upon support of a cloud based backend system.

It should be understood that once in the current user's AR/VR computing environment (AR/VR) with the AR/VR device running the computing necessary to generate the AR/VR, the system may make a further "switching" recommendation to switch back to RR reality. In response to this "switch" recommendation being made, the AR/VR device is commanded to stop displaying the AR/VR objects.

Continuing, to step 430, FIG. 4, within the changed user's environment (e.g., AR or VR) for performing the same or similar task, the physiological evaluation and task efficiency monitoring modules are invoked to determine the user's task efficiency when performing various tasks in the changed AR/VR environment.

The user performs that same or a similar task in the new environment, and at 440, a determination is made as to whether the user performance of the same task has increased, i.e., is performed with greater efficiency in the new environment. An example criteria for determining that the user has/has not been able to improve over the low task efficient score is whether the user has had a score below a threshold X for a certain period of time, and/or the user's score has not changed more than a threshold Y % when compared to immediate prior user scores.

This may be determined by comparing the user's current efficiency score with the previously user task efficiency score (over time) to determine if there is any improvement after user has performed the task in the VR or AR environments.

In one embodiment, if it is determined that the user's task efficiency has not improved in the switched environment, then system may continuously monitor the user's task efficiency and physiological/emotion state in RR and determines if there is any improvement over the task efficiency when running the task in VR/AR. The system stores this data for later usage either for the user, or for crowd sourcing.

Thus, from 440, FIG. 4, the system may return to step 420 where the reality switching module may provide another suggestion to switch to a same or alternative AR/VR or RR reality and perform the same or another similar task for task efficiency and physiological/emotion state monitoring. This suggestion could be based on historical improvements in efficiency and/or mood as obtained from crowd sourced data or data related to that particular user. In this manner, the system may repeat the steps 425, 430, 440 until the user exhibits increased efficiency for that particular task.

In this process, the system will record the user's scores over time along with VR/AR activities that user has performed to determine if there is any correlation of using VR or AR to improve the user's task efficiency score. Additionally recorded for purposes of recommending may include information pertaining to the time length of help from VR sessions per a given task type and/or record the number of VR/AR sessions per a given task type.

At 440, once it is determined that the user's efficiency for performing the particular task has improved (e.g., the task efficiency score increases above a determined threshold), then the process may end.

In one embodiment, when determined that the user's efficiency has increased for that task, then each of the tasks performed by the user, the reality environments in which the tasks were performed within, and the determined efficiency scores of that user in each reality environment are stored in a memory storage device, e.g., in a historical database 330, so that this information may be subsequently used as crowd sourced data for the benefit of the same and/or other users who's efficiency for performing same or similar tasks is to be improved.

That is, when that same user later performs a same task, the system 300 will provide another AR/VR suggestion, based on historical improvements in efficiency and/or mood.

FIG. 5 depicts a table 500 showing example variables and values appurtenant to the non-limiting example scenario described above with respect to FIGS. 2A and 2B.

For the example context scenario switch depicted in the example described herein above with respect to FIGS. 2A, 2B, as shown in FIG. 5, a variable "Context Scenario" 505 may be populated by the Reality Switching module 335 for use coordinating the recommendation to switch from the business report generating task from (real) reality to performing the task in an augmented reality (e.g., the coffee shop).

Further, as shown in FIG. 5, a variable "Augmented_Contents" 510 may be populated by the Reality Switching module 335 for use in suggesting the type of reality augmentation recommended. In the illustrative example of FIGS. 2A, 2B, this variable may indicate the generation of coffee and the business revenue goal for the recommended augmented reality environment.

Further, as shown in FIG. 5, a variable "Insert_Time" 515 may be populated by the Reality Switching module 335 for use in recording when the conversation has been started between the meeting attendees at the (e.g., augmented) meeting location. For the illustrative example of FIGS. 2A, 2B, a further "Meeting_Attendees" variable 520 may be populated with values such as User A and User B who are meeting in the augmented environment in the example. A further "Meeting_Location" variable 525 may be populated with a value such as the "coffee shop" which is the recommended augmented reality computing environment to be switched to in the illustrative example. A further "Meeting_Content" variable 530 may be populated with a value such as the "User A's Business Report" which is the object of the task recommended to be performed within the augmented reality computing environment to be switched to in the illustrative example.

Further, as shown in FIG. 5, a variable "Measured_Task_efficiency_in_AR" 535 may be populated by the Task Monitoring Module 340 for use in recording a measured time it took the user to finish the business report (e.g., 1.5 days) and the corresponding overall business report review result task evaluation score from a supervisor (e.g., an example score of "85"). The variable "Historical_Task_Efficiency_in_RR_from_history" 540 may be populated by the Task Monitoring Module 340 to obtain for comparison purposes in measuring a task efficiency, a historical measure of efficiency. For example, this variable will represent the average historical measured time it took this user (or other users) to finish the business report (e.g., 2.0 days) and the corresponding overall business report review result task evaluation score from a supervisor (e.g., an example score of "70").

Further, as shown in FIG. 5, a variable "UserID" 545 is provided that may be populated in order to identify the user who is to be recommended a reality switch change, e.g., from real reality to one of: a virtual reality or augmented reality (computing environment) as was recommended to UserA for example, in the illustrative example of FIGS. 2A, 2B.

Further, as shown in FIG. 5, a variable "Remove_AR_VR Contents" 550 may be asserted by the system when meeting attendees leave the augmented environment meeting or virtual environment meeting location or switch to other content than the meeting content.

Further, as shown in FIG. 5, a variable "Should AR Used" 555 or "Should VR Used" 560 may be asserted by the Reality Switching module 335 for use in suggesting to the user which reality computing environment to switch to. In the illustrative example of FIGS. 2A, 2B, the variable "Should AR Used" 555 was populated with a "yes" value in order to effect the recommending of switching of the current environment to the AR computing environment, while the variable "Should VR Used" 560 may be populated with a "no" value.

Further, as shown in FIG. 5, a variable "Recommend AR In-Future_For_This Context" 565 may be asserted by the Reality Switching module 335 for use in recording the current AR recommendation and any corresponding determined task efficiency improvements for future use in recommending switched reality environments for other user's faced with similar scenario/context. Likewise, the variable "Recommend VR In-Future_For_This Context" 570 may be asserted by the Reality Switching module 335 for use in recording the current VR recommendation and any corresponding determined task efficiency improvements for future use in recommending switched reality environments for other user's faced with similar scenario/context. For the illustrative example of FIGS. 2A, 2B, the variable "Recommend AR In-Future_For_This Context" 565 may be populated with a "yes" value in order to ensure recording, for future recommendations, the current recommending of the switching of the reality computing environment to the AR computing environment in the illustrative example. In this example, the "Recommend VR In-Future_For_This Context" may be populated with a "no" value as no switching of the reality computing environment to the VR computing environment was recommended in the illustrative example.

The system and methods described herein are configured as an intelligent recommendation tool configured to suggest to users to perform various tasks in different reality systems to help user to maximize their productivity and achieve better satisfaction, happiness and health. That is, attempting to do a given task well in VR/AR computing environment is great training and will boost user's skill and confidence to do the task or similar task in real reality. Attempting to do a given task well in a VR computing environment brings a user great satisfaction, especially when user isn't physically capable to do the task in real reality. Further, a user's mood, happiness and health is improved.

Figure 6:
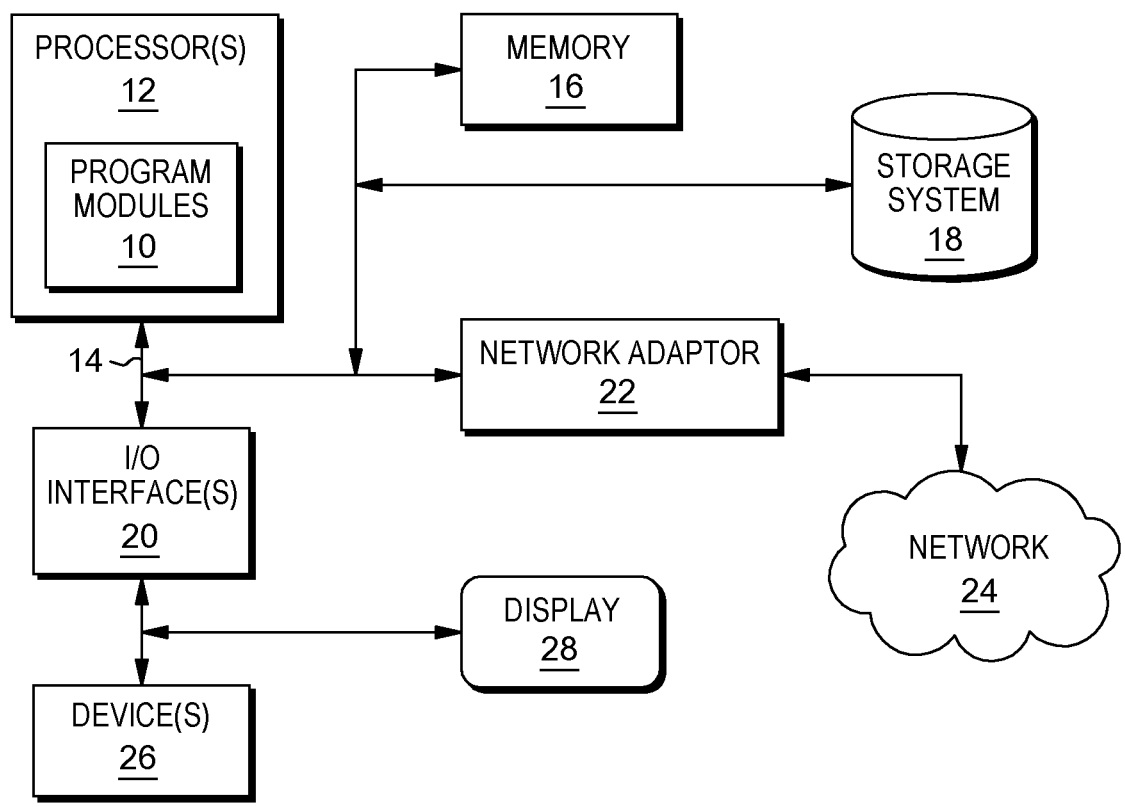
FIG. 6 depicts a schematic of an example computing system configurable for running the system and method embodiments of the present disclosure.

FIG. 6 illustrates an example computing system in accordance with the present invention that may provide the services and functions associated with intelligent recommendations to switch realities. It is to be understood that the computer system depicted is only one example of a suitable processing system and is not intended to suggest any limitation as to the scope of use or functionality of embodiments of the present invention. For example, the system shown may be operational with numerous other general-purpose or special-purpose computing system environments or configurations. Examples of well-known computing systems, environments, and/or configurations that may be suitable for use with the system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In some embodiments, the computer system may be described in the general context of computer system executable instructions, embodied as program modules stored in memory 16, being executed by the computer system. Generally, program modules may include routines, programs, objects, components, logic, data structures, and so on that perform particular tasks and/or implement particular input data and/or data types in accordance with the methods described in FIG. 4.

The components of the computer system may include, but are not limited to, one or more processors or processing units 12, a memory 16, and a bus 14 that operably couples various system components, including memory 16 to processor 12. In some embodiments, the processor 12 may execute one or more modules 10 that are loaded from memory 16, where the program module(s) embody software (program instructions) that cause the processor to perform one or more method embodiments of the present invention. In some embodiments, module 10 may be programmed into the integrated circuits of the processor 12, loaded from memory 16, storage device 18, network 24 and/or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

Memory 16 (sometimes referred to as system memory) can include computer readable media in the form of volatile memory, such as random access memory (RAM), cache memory an/or other forms. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with the computer system; and/or any devices (e.g., network card, modem, etc.) that enable the computer system to communicate with one or more other computing devices. Such communication can occur via Input/Output (I/O) interfaces 20.

Still yet, the computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A task recommender tool comprising:
a memory storage system storing program instructions;
a processor for running said stored program instructions to configure the processor to:
detect a user's task efficiency in performing a task in a current real environment, the task comprising an interest vector having a topic or keyword of interest mined from a user's personal data store;
compute a task efficiency score based on a combination of: a length of time it takes to perform the task, the numbers of errors and/or failures when performing the task, the number of pauses or interruptions taken, and a number of task completion results;
recommend, based on a results of said task efficiency detecting in the current real environment while the user engages in a topic or keyword of said interest vector, a switch from a current real environment to one of: a virtual reality computing environment or an augmented reality computer environment;
recommend the same task to be performed in the switched virtual reality computing environment or augmented reality computing environment, wherein upon switching to the switched computing environment, the user performs the same recommended task in the switched environment;
determine whether the user's efficiency in performing the same task has increased in the switched environment, said determining comprising:
comparing a user's task efficiency score from performing the same task in the current or switched computing environment against that user's task efficiency score from performing the same task in a prior real computing or switched computing environment to determine whether the user's efficiency in performing the task has increased; and
repeat said user task efficiency detecting when in each subsequent real or a switched environment while the user performs the same recommended task in the real or switched environment until the user's task efficiency has improved.

2. The task recommender tool as claimed in claim 1, wherein the processor is further configured to:
detect the user's emotional state while performing the same task;
recommend, based on a results of said emotional state detecting, a computing environment switch from a current real environment to one of: a virtual reality computing environment or an augmented reality computer environment;
recommend a task to performed in the switched computing environment, wherein upon switching to a switched computing environment, the user performs the same recommended task in the switched environment;
determining whether the user's emotional state has been elevated; and
repeating said emotional state detecting in each subsequent real or a switched environment while the user performs the same recommended task in the real or switched environment until the user's emotional state has been elevated.

3. The task recommender tool as claimed in claim 2, wherein the processor is further configured to:

control an audio, video or audio/video sensor to monitor and record the user's behavior while performing the same task; and
use the recorded audio, video or audio/video to determine that user's emotional state while performing the same task in the current or switched reality environment.

4. The task recommender tool as claimed in claim 3, wherein the processor is further configured to:
conduct a voice analysis on said recorded audio to determine that user's emotional state while performing the same task in the current or switched reality environment.

5. The task recommender tool as claimed in claim 2, wherein the processor is further configured to:
analyze that user's messages or that user's social media comments/updates communicated over a communications network to determine that user's emotional state while performing the same task in the current or switched reality environment.

6. The task recommender tool as claimed in claim 2, wherein the processor is further configured to:
record, in a memory storage device, data corresponding to the user's task efficiency determinations in any environment in which a task is performed by that user;
record, in the memory storage device, data corresponding to which tasks were performed and the resulting determined environment switch recommendations and tasks performed in those switched environments that resulted in increased user efficiency or elevated emotional state when performing the task; and
use historical recorded task efficiency data, recommended tasks performed, and switched environment recommendations to recommend to a current user which computing environment to switch to and which task to recommend.

7. The task recommender tool as claimed in claim 2, wherein the processor is further configured to:
for multiple users:
record, in a memory storage device, data corresponding to each user's task efficiency determinations in any environment in which a task is performed by each multiple user;
record, in the memory storage device, data corresponding to which tasks were performed and the resulting determined environment switch recommendations and tasks performed in those switched environments that resulted in increased efficiency in performing the task for each multiple user or elevated the user's emotional state when performing the task; and
use historical recorded task efficiency data, recommended tasks performed, and switched environment recommendations for the multiple users to recommend to a current user which computing environment to switch to and which task to recommend.

8. The task recommender tool as claimed in claim 1, wherein the processor is further configured to:
record information comprising a user's scores over time along with associated tasks performed in the switched computing environment;
determine, based on recorded scores, whether there is any correlation of using the switched computing environment to improve the user's task efficiency score.

9. The task recommender tool as claimed in claim 8, wherein the processor is further configured to:
record further information comprising a length of help received when performing a given task type from in the switched computing environment; and a number of sessions performed in the switched computing environment per a given task type.

10. The task recommender tool as claimed in claim 9, wherein the processor is further configured to:
provide the recorded information and recorded further information as crowd sourcing data; and
based on the crowd sourcing data provided, one or more of:
checking if a suggestion of performing the task or another task in the switched computing environment actually helped for a given type of user and to what degree of help; or
checking when a user can perform the task effectively without help from performing the task in the switched computing environment.

11. A method for recommending tasks for a user to perform comprising:
detecting, by a processor, a user's task efficiency in performing a task in a current real environment, the task comprising an interest vector having a topic or keyword of interest mined from a user's personal data store;
computing, using the processor, a task efficiency score based on a combination of: a length of time it takes to perform the task, the numbers of errors and/or failures when performing the task, the number of pauses or interruptions taken, and a number of task completion results;
using the processor to recommend, based on a results of said task efficiency detecting in the current real environment while the user engages in a topic or keyword of said interest vector, a switch from the current real environment to one of: a virtual reality computing environment or an augmented reality computer environment;
using the processor to recommend the same task to be performed in the switched virtual reality computing environment or augmented reality computing environment, wherein upon switching to the switched computing environment, the user performs the same recommended task in the switched environment;
determining, using the processor, whether the user's efficiency in performing the same task has increased in the switched environment, said determining comprising:
comparing a user's task efficiency score from performing the same task in the current or switched computing environment against that user's task efficiency score from performing the same task in a prior real computing or switched computing environment to determine whether the user's efficiency in performing the task has increased; and
repeating said user task efficiency detecting when in each subsequent real or a switched environment while the user performs the same recommended task in the real or switched environment until the user's task efficiency has improved.

12. The method as claimed in claim 11, further comprising:
detecting, using the processor, the user's emotional state while performing the same task;
using the processor to recommend, based on a results of said emotional state detecting, a computing environment switch from a current real environment to one of: a virtual reality computing environment or an augmented reality computer environment;
recommending, using the processor, a task to performed in the switched computing environment, wherein upon switching to a switched computing environment, the user performs the same recommended task in the switched environment;

determining, using the processor, whether the user's emotional state has been elevated; and repeating said emotional state detecting in each subsequent real or a switched environment while the user performs the same recommended task in the real or switched environment until the user's emotional state has been elevated.

13. The method claimed in claim 12, further comprising:

using the processor to control an audio, video or audio/video sensor to monitor and record the user's behavior while performing the task; and using, by the processor, the recorded audio, video or audio/video to determine that user's emotional state while performing the task in the current or switched reality environment.

14. The method as claimed in claim 13, further comprising:

using the processor to conduct a voice analysis on said recorded audio to determine that user's emotional state while performing the same task in the current or switched reality environment.

15. The method as claimed in claim 12, further comprising:

using the processor to analyze that user's messages or that user's social media comments/updates communicated over a communications network to determine that user's emotional state while performing the same task in the current or switched reality environment.

16. The method as claimed in claim 12, further comprising:

record, in a memory storage device, data corresponding to the user's task efficiency determinations in any environment in which a task is performed by that user;

record, in the memory storage device, data corresponding to which tasks were performed and the resulting determined environment switch recommendations and tasks performed in those switched environments that resulted in increased user efficiency or elevated emotional state when performing the task; and use historical recorded task efficiency data, recommended tasks performed, and switched environment recommendations to recommend to a current user which computing environment to switch to and which task to recommend; or for multiple users:

record, in a memory storage device, data corresponding to each user's task efficiency determinations in any environment in which a task is performed by each multiple user;

record, in the memory storage device, data corresponding to which tasks were performed and the resulting determined environment switch recommendations and tasks performed in those switched environments that resulted in increased efficiency in performing the task for each multiple user or elevated the user's emotional state when performing the task; and use historical recorded task efficiency data, recommended tasks performed, and switched environment recommendations for the multiple users to recommend to a current user which computing environment to switch to and which task to recommend.

17. A non-transitory computer readable medium comprising instructions that, when executed by at least one processor comprising hardware, configure the at least one processor to:

detect a user's task efficiency in performing a task in a current real environment, the task comprising an interest vector having a topic or keyword of interest mined from a user's personal data store;

compute a task efficiency score based on a combination of: a length of time it takes to perform the task, the numbers of errors and/or failures when performing the task, the number of pauses or interruptions taken, and a number of task completion results;

recommend, based on a results of said task efficiency detecting in the current real environment while the user engages in a topic or keyword of said interest vector, a switch from a current real environment to one of: a virtual reality computing environment or an augmented reality computer environment;

recommend the same task to be performed in the switched virtual reality computing environment or augmented reality computing environment, wherein upon switching to the switched computing environment, the user performs the same recommended task in the switched environment;

determine whether the user's efficiency in performing the same task has increased in the switched environment, said determining comprising:

comparing a user's task efficiency score from performing the same task in the current or switched computing environment against that user's task efficiency score from performing the same task in a prior real computing or switched computing environment to determine whether the user's efficiency in performing the task has increased; and repeat said user task efficiency detecting when in each subsequent real or a switched environment while the user performs the same recommended task in the real or switched environment until the user's task efficiency has improved.

18. The computer readable medium as claimed in claim 17, wherein the instructions further configure the at least one processor to:

detect the user's emotional state while performing the same task;

recommend, based on a results of said emotional state detecting, a computing environment switch from a current real environment to one of: a virtual reality computing environment or an augmented reality computer environment;

recommend a task to performed in the switched computing environment, wherein upon switching to a switched computing environment, the user performs the same recommended task in the switched environment, determine whether the user's emotional state has been elevated, and repeat said emotional state detecting in each subsequent real or a switched environment while the user performs the same recommended task in the real or switched environment until the user's emotional state has been elevated.

19. The computer readable medium as claimed in claim 18, wherein the instructions further configure the at least one processor to:

control an audio, video or audio/video sensor to monitor and record the user's behavior while performing the task, and use the recorded audio, video or audio/video to determine that user's emotional state while performing the same task in the current or switched reality environment, or analyze that user's messages or that user's social media comments/updates communicated over a communications network to determine that user's emotional state while performing the same task in the current or switched reality environment.

20. The computer readable medium as claimed in claim 18, wherein the instructions further configure the at least one processor to:

record, in a memory storage device, data corresponding to the user's task efficiency determinations in any environment in which a task is performed by that user;

record, in the memory storage device, data corresponding to which tasks were performed and the resulting determined environment switch recommendations and tasks performed in those switched environments that resulted in increased user efficiency or elevated emotional state when performing the task; and use historical recorded task efficiency data, recommended tasks performed, and switched environment recommendations to recommend to a current user which computing environment to switch to and which task to recommend; or for multiple users:

record, in a memory storage device, data corresponding to each user's task efficiency determinations in any environment in which a task is performed by each multiple user;

record, in the memory storage device, data corresponding to which tasks were performed and the resulting determined environment switch recommendations and tasks performed in those switched environments that resulted in increased efficiency in performing the task for each multiple user or elevated the user's emotional state when performing the task; and use historical recorded task efficiency data, recommended tasks performed, and switched environment recommendations for the multiple users to recommend to a current user which computing environment to switch to and which task to recommend.

* * * * *